(12) United States Patent
Abdulhafez et al.

(10) Patent No.: US 11,565,025 B1
(45) Date of Patent: Jan. 31, 2023

(54) SURFACE ENHANCED DEMINERALIZED BONE GRAFT MATERIAL

(71) Applicant: Progenica Therapeutics, LLC, Kent, WA (US)

(72) Inventors: Abdulhafez Abdulwahed Abdulhafez, Hickory Hill, TN (US); Helen Newman, Seattle, WA (US); Lawrence Shimp, Burlington, WI (US)

(73) Assignee: PROGENICA THERAPEUTICS, LLC, Kent, WA (US)

( * ) Notice: Subject to any disclaimer, the term of this patent is extended or adjusted under 35 U.S.C. 154(b) by 251 days.

(21) Appl. No.: 15/687,199

(22) Filed: Aug. 25, 2017

(51) Int. Cl.
| | | |
|---|---|---|
| *A61L 27/54* | (2006.01) | |
| *A61L 27/36* | (2006.01) | |
| *A61L 27/34* | (2006.01) | |
| *A61L 27/58* | (2006.01) | |
| *A61L 27/56* | (2006.01) | |
| *A61L 27/26* | (2006.01) | |

(52) U.S. Cl.
CPC .............. *A61L 27/54* (2013.01); *A61L 27/26* (2013.01); *A61L 27/34* (2013.01); *A61L 27/365* (2013.01); *A61L 27/3608* (2013.01); *A61L 27/56* (2013.01); *A61L 27/58* (2013.01); *A61L 2300/252* (2013.01); *A61L 2300/414* (2013.01); *A61L 2300/606* (2013.01); *A61L 2430/02* (2013.01)

(58) Field of Classification Search
None
See application file for complete search history.

(56) References Cited

U.S. PATENT DOCUMENTS

| | | |
|---|---|---|
| 7,132,506 B2 | 11/2006 | Nishimura et al. |
| 7,754,683 B2 | 7/2010 | Guo et al. |
| 7,897,163 B2 | 3/2011 | Park et al. |
| 8,062,890 B2 | 11/2011 | Kiessling et al. |
| 8,075,562 B2 | 12/2011 | Murphy et al. |
| 8,420,774 B2 | 4/2013 | Murphy et al. |
| 8,642,337 B2 | 2/2014 | Kiessling et al. |
| 8,778,869 B2 | 7/2014 | Murphy et al. |
| 8,846,860 B2 | 9/2014 | Murphy et al. |
| 8,853,164 B2 | 10/2014 | Kang et al. |

FOREIGN PATENT DOCUMENTS

| | | |
|---|---|---|
| EP | 1288228 B1 | 5/2006 |
| EP | 2540739 B1 | 10/2015 |

OTHER PUBLICATIONS

Zhao et al. (Journal of Controlled Release 141 (2010) 30-37) (Year: 2010).*
Huber et al. (Tissue Eng Part A. Dec. 2017;23(23-24):1321-1330. Epub Apr. 28, 2017) (Year: 2017).*
Tran et al. (Bioconjugate Chem. 2007, 18, 549-558) (Year: 2007).*
Zhong et al. (Bone Research (2015) 3, 15013) (Year: 2015).*
Horvathy et al. (Biofactors. May 6, 2017;43(3):315-330. doi: 10.1002/biof.1337. Epub Nov. 11, 2016) (Year: 2016).*
Dasari et al. (Chembiochem. 18(18): 1792-1796; Epub Aug. 10, 2017) (Year: 2017).*

* cited by examiner

*Primary Examiner* — Sergio Coffa
(74) *Attorney, Agent, or Firm* — Dorsey & Whitney LLP

(57) ABSTRACT

Described herein are compositions comprising a BMP-2 derived peptide conjugated to albumin for use in bone grafts. The composition may further include bone matrix, such as demineralized bone matrix (DBM).

26 Claims, 7 Drawing Sheets
(6 of 7 Drawing Sheet(s) Filed in Color)
Specification includes a Sequence Listing.

\>sp|P12643|283-396

QAKHKQRKRLKSSCKRHPLYVDFSDVGWNDWIVAPPGYHAFYCHGECPFPLADHLNSTNH

AIVQTLVNSVNSKIPKACCVPTELSAISMLYLDENEKVVLKNYQDMVVEGCGCR

Fig. 4

Fig. 5
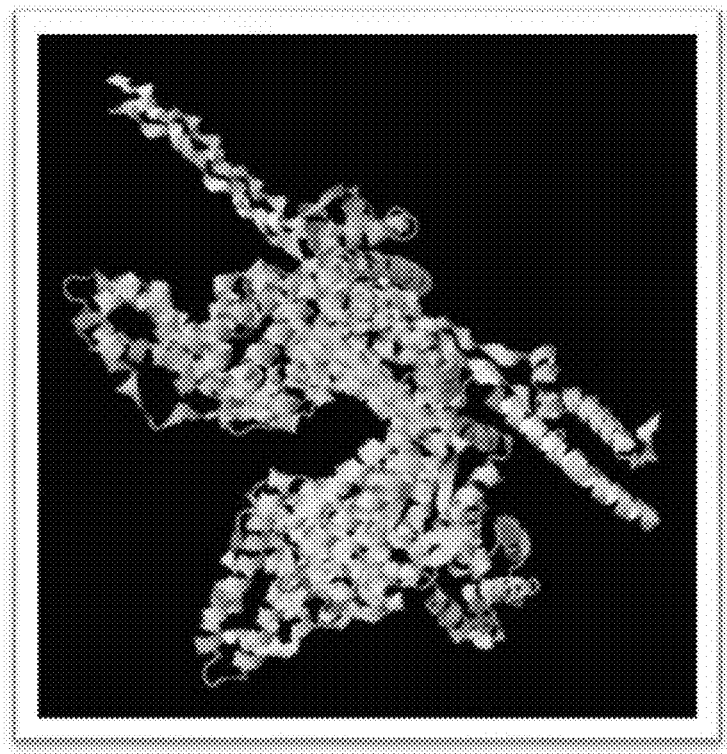
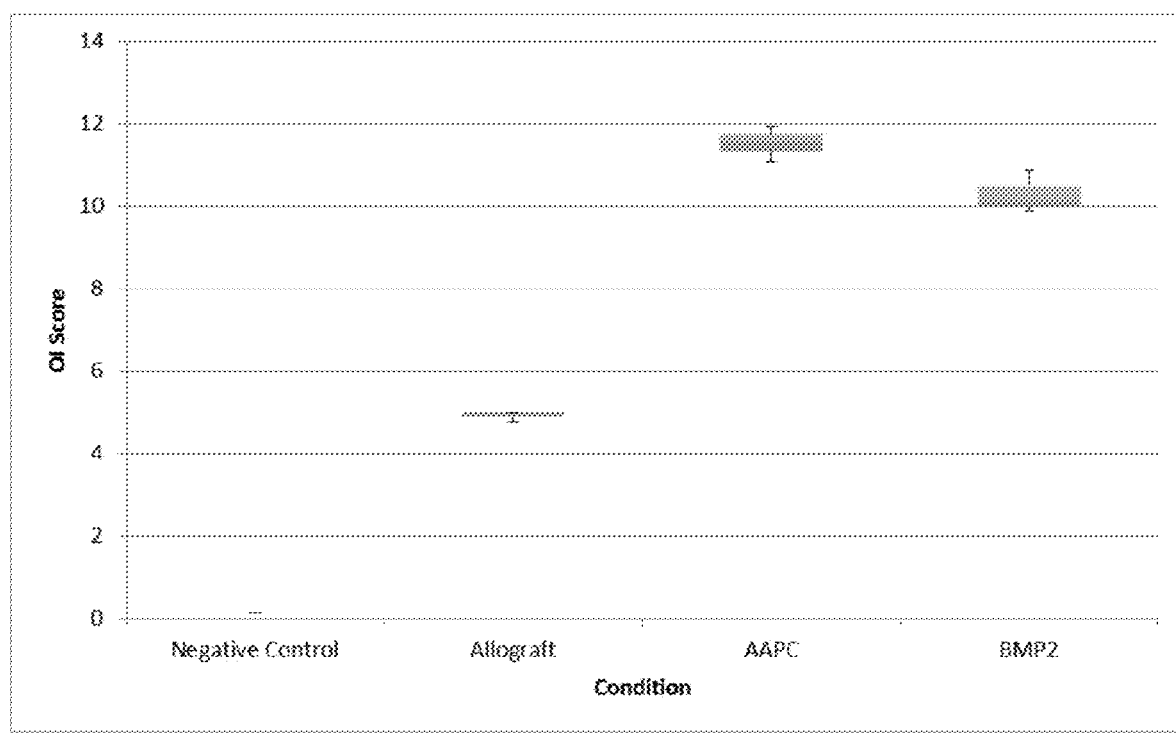
Fig. 6

SEQUENCE LISTING

<160> NUMBER OF SEQ ID NOS: 14

<210> SEQ ID NO 1
<211> LENGTH: 44
<212> TYPE: PRT
<213> ORGANISM: Artificial Sequence
<220> FEATURE:
<223> OTHER INFORMATION: Synthetic peptide

<400> SEQUENCE: 1

Cys Gly Gly Gly Val Asn Ser Lys Ile Pro Lys Ala Cys Cys Val Pro
 1               5                  10                  15

Thr Glu Leu Ser Ala Ile Ser Met Leu Tyr Leu Asp Glu Asn Glu Lys
            20                  25                  30

Val Val Leu Lys Asn Tyr Gln Asp Met Val Val Glu
        35                  40

<210> SEQ ID NO 2
<211> LENGTH: 24
<212> TYPE: PRT
<213> ORGANISM: Artificial Sequence
<220> FEATURE:
<223> OTHER INFORMATION: Synthetic peptide

<400> SEQUENCE: 2

Cys Gly Gly Gly Lys Ile Pro Lys Ala Ser Ser Val Pro Thr Glu Leu
 1               5                  10                  15

Ser Ala Ile Ser Thr Leu Tyr Leu
            20

<210> SEQ ID NO 3
<211> LENGTH: 29
<212> TYPE: PRT
<213> ORGANISM: Artificial Sequence
<220> FEATURE:
<223> OTHER INFORMATION: Synthetic peptide

<400> SEQUENCE: 3

Cys Gly Gly Gly Ser Ala Ile Ser Met Leu Tyr Leu Asp Glu Asn Glu
 1               5                  10                  15

Lys Val Val Leu Lys Asn Tyr Gln Asp Met Val Val Glu
            20                  25

<210> SEQ ID NO 4
<211> LENGTH: 41
<212> TYPE: PRT
<213> ORGANISM: Artificial Sequence
<220> FEATURE:
<223> OTHER INFORMATION: Synthetic peptide

<400> SEQUENCE: 4

Cys Gly Gly Gly Lys Ile Pro Lys Ala Ala Ala Val Pro Thr Glu Leu
 1               5                  10                  15

Ser Ala Ile Ser Met Leu Tyr Leu Asp Glu Asn Glu Lys Val Val Leu
            20                  25                  30

Lys Asn Tyr Gln Asp Met Val Val Glu
        35                  40

<210> SEQ ID NO 5
<211> LENGTH: 24
<212> TYPE: PRT
<213> ORGANISM: Artificial Sequence
<220> FEATURE:
<223> OTHER INFORMATION: Synthetic peptide

<400> SEQUENCE: 5

Cys Gly Gly Gly Lys Ile Pro Lys Ala Ala Ala Val Pro Thr Glu Leu
1               5                   10                  15

Ser Ala Ile Ser Thr Leu Tyr Leu
            20

<210> SEQ ID NO 6
<211> LENGTH: 24
<212> TYPE: PRT
<213> ORGANISM: Artificial Sequence
<220> FEATURE:
<223> OTHER INFORMATION: Synthetic peptide

<400> SEQUENCE: 6

Cys Gly Gly Gly Lys Ile Pro Lys Ala Gly Ser Val Pro Thr Glu Leu
1               5                   10                  15

Ser Ala Ile Ser Thr Leu Tyr Leu
            20

<210> SEQ ID NO 7
<211> LENGTH: 24
<212> TYPE: PRT
<213> ORGANISM: Artificial Sequence
<220> FEATURE:
<223> OTHER INFORMATION: Synthetic peptide

<400> SEQUENCE: 7

Cys Gly Gly Gly Lys Ile Pro Lys Ala Ser Gly Val Pro Thr Glu Leu
1               5                   10                  15

Ser Ala Ile Ser Thr Leu Tyr Leu
            20

<210> SEQ ID NO 8
<211> LENGTH: 41
<212> TYPE: PRT
<213> ORGANISM: Artificial Sequence
<220> FEATURE:
<223> OTHER INFORMATION: Synthetic peptide

<400> SEQUENCE: 8

Cys Gly Gly Gly Lys Ile Pro Lys Ala Gly Gly Val Pro Thr Glu Leu
1               5                   10                  15

Ser Ala Ile Ser Met Leu Tyr Leu Asp Glu Asn Glu Lys Val Val Leu
            20                  25                  30

Lys Asn Tyr Gln Asp Met Val Val Glu
        35                  40

<210> SEQ ID NO 9
<211> LENGTH: 41
<212> TYPE: PRT
<213> ORGANISM: Artificial Sequence
<220> FEATURE:
<223> OTHER INFORMATION: Synthetic peptide

<400> SEQUENCE: 9

Cys Gly Gly Gly Lys Ile Pro Lys Ala Gly Ser Val Pro Thr Glu Leu
1               5                   10                  15

Ser Ala Ile Ser Met Leu Tyr Leu Asp Glu Asn Glu Lys Val Val Leu
            20                  25                  30

Lys Asn Tyr Gln Asp Met Val Val Glu
        35                  40

```
<210> SEQ ID NO 10
<211> LENGTH: 41
<212> TYPE: PRT
<213> ORGANISM: Artificial Sequence
<220> FEATURE:
<223> OTHER INFORMATION: Synthetic peptide

<400> SEQUENCE: 10

Cys Gly Gly Gly Lys Ile Pro Lys Ala Ser Gly Val Pro Thr Glu Leu
1               5                   10                  15

Ser Ala Ile Ser Met Leu Tyr Leu Asp Glu Asn Glu Lys Val Val Leu
            20                  25                  30

Lys Asn Tyr Gln Asp Met Val Val Glu
        35                  40

<210> SEQ ID NO 11
<211> LENGTH: 44
<212> TYPE: PRT
<213> ORGANISM: Artificial Sequence
<220> FEATURE:
<223> OTHER INFORMATION: Synthetic peptide

<400> SEQUENCE: 11

Cys Gly Gly Gly Val Asn Ser Lys Ile Pro Lys Ala Cys Cys Val Pro
1               5                   10                  15

Thr Glu Leu Ser Ala Ile Ser Met Leu Tyr Leu Asp Glu Asn Glu Lys
            20                  25                  30

Val Val Leu Lys Asn Tyr Gln Asp Met Val Val Glu
            35                  40

<210> SEQ ID NO 12
<211> LENGTH: 41
<212> TYPE: PRT
<213> ORGANISM: Artificial Sequence
<220> FEATURE:
<223> OTHER INFORMATION: Synthetic peptide

<400> SEQUENCE: 12

Cys Gly Gly Gly Lys Ile Pro Lys Ala Cys Cys Val Pro Thr Glu Leu
1               5                   10                  15

Ser Ala Ile Ser Met Leu Tyr Leu Asp Glu Asn Glu Lys Val Val Leu
            20                  25                  30

Lys Asn Tyr Gln Asp Met Val Val Glu
        35                  40

<210> SEQ ID NO 13
<211> LENGTH: 609
<212> TYPE: PRT
<213> ORGANISM: Artificial Sequence
<220> FEATURE:
<223> OTHER INFORMATION: Recombinant Protein

<400> SEQUENCE: 13

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60
```

```
Lys Leu Val Asn Glu Val Thr Glu Phe Ala Lys Thr Cys Val Ala Asp
 65                  70                  75                  80

Glu Ser Ala Glu Asn Cys Asp Lys Ser Leu His Thr Leu Phe Gly Asp
             85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
            115                 120                 125

His Lys Asp Asp Asn Pro Asn Leu Pro Arg Leu Val Arg Pro Glu Val
        130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
        210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
        450                 455                 460

Pro Glu Ala Lys Arg Met Pro Cys Ala Glu Asp Tyr Leu Ser Val Val
465                 470                 475                 480
```

```
Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
            530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
            565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
            595                 600                 605

Leu

<210> SEQ ID NO 14
<211> LENGTH: 396
<212> TYPE: PRT
<213> ORGANISM: Homo sapiens

<400> SEQUENCE: 14

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
                20                  25                  30

Phe Ala Ala Ala Ser Ser Gly Arg Pro Ser Ser Gln Pro Ser Asp Glu
            35                  40                  45

Val Leu Ser Glu Phe Glu Leu Arg Leu Leu Ser Met Phe Gly Leu Lys
        50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
        210                 215                 220

Gly Phe Val Val Glu Val Ala His Leu Glu Glu Lys Gln Gly Val Ser
225                 230                 235                 240
```

```
Lys Arg His Val Arg Ile Ser Arg Ser Leu His Gln Asp Glu His Ser
            245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
            275                 280                 285

Arg Lys Arg Leu Lys Ser Ser Cys Lys Arg His Pro Leu Tyr Val Asp
        290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
                340                 345                 350

Asn Ser Lys Ile Pro Lys Ala Cys Cys Val Pro Thr Glu Leu Ser Ala
            355                 360                 365

Ile Ser Met Leu Tyr Leu Asp Glu Asn Glu Lys Val Val Leu Lys Asn
        370                 375                 380

Tyr Gln Asp Met Val Val Glu Gly Cys Gly Cys Arg
385                 390                 395
```

SURFACE ENHANCED DEMINERALIZED BONE GRAFT MATERIAL

FIELD

The disclosed processes, methods, and systems are directed to grafting bone with a high degree of safety and effectiveness. The method relies on a graft material that acts as a scaffold with enhanced osteoinductive (OI) activity that does not extend beyond the graft site.

SEQUENCE LISTING

A sequence listing submitted in computer readable format is hereby incorporated by reference. The computer readable file is named P267344_US_01_ST25.txt, was created on Aug. 25, 2017, and contains 14 kilobytes.

BACKGROUND

Bone heals better than any other organ system, but in the case of severe injuries, it still can benefit from additional therapeutic interventions. Bone can heal gaps up to about 1 mm wide; beyond that there is a risk that the bone will be replaced by fibrous tissue resulting in a non-union. The typical approach is to add a material (scaffold) to the defect that bone cells adhere to and grow on. With such a strategy, gaps of 10 to 20 mm or more can be bridged and healed. However, bone healing using just a synthetic scaffold or even Demineralized Bone Matrix (DBM) can be quite slow. In order to speed up healing, one strategy is to add a growth factor (BMP-2) that stimulates the activity of the bone-forming cells to speed the formation of bone as well as encourage the disappearance (resorption) of the scaffold.

A commercially available example of a product containing a manufactured BMP-2 growth factor is INFUSE from Medtronic. This product contains recombinant bone morphogenic protein 2 (BMP-2) that is combined with a collagen sponge (bovine tendon source). The BMP-2 is made using recombinant technologies wherein a gene for BMP-2 is inserted into mammalian cells which then are induced to produce large quantities of the protein into the surrounding solution. Application in high concentrations of BMP-2 (INFUSE) can cause a dramatic increase in the rate of bone healing (up to a five-fold factor). But it is not bound to the scaffold, and so is free to migrate away after implantation. This has led to unwanted side effects such as bone growing in surrounding tissues which, in turn, has caused injury or even death to some patients. Other side effects include inflammation, seroma, swelling and radiculopathy.

What is needed is a synthetic peptide, bound to the scaffold that can be collagen but is preferably DBM, as the signaling molecule. Disclosed herein is a peptide that may comprise only an active part of the BMP-2 growth factor protein, and a chemical group attached to the peptide that will bond the peptide to the collagen carrier or the collagen in the DBM scaffold. Because it is immobilized on the surface of the carrier, the peptide cannot leave the graft site—it is intrinsically part of the scaffold. This, combined with the completely synthetic origin of the peptide gives it a substantially improved safety profile compared to the existing product (INFUSE). Furthermore, unlike the intrinsic BMPs in demineralized bone alone, the amount of bound active peptide can be increased to a high level so that bone healing performance will be many times faster than what can be obtained with un-augmented demineralized bone. In addition, the product should be easy to use, requiring no special preparation or surgical procedures on the part of the user.

SUMMARY

Disclosed herein is a method for adding BMP-2 growth factor activity to collagen based bone grafts, preferably consisting of DBM, in order to increase the effectiveness of the graft as a bone healing scaffold. Also disclosed are methods for tendon and ligament grafting using the disclosed compositions. Demineralized Bone Matrix, DBM, was the first commercially available product to incorporate growth factor proteins which are naturally present in bone and are activated by the demineralization process. DBM has been proven to be safe and effective, and is still used in many situations. However, the bone grafting market is now dominated by INFUSE from Medtronic.

INFUSE contains a recombinant bone morphogenic protein, (BMP-2). BMP-2 is one of the growth factors present in DBM but the availability of the recombinant form means that it can be added to a bone scaffold in far higher concentrations that are naturally occurring in DBM. The BMP is made using recombinant technologies wherein a gene for BMP-2 is inserted into bacteria or mammalian cells which then are induced to produce large quantities of the protein into the surrounding solution from which it is recovered and purified.

In use, the BMP-2 is applied to a collagen sponge during the surgical procedure. Unlike the proteins in DBM, the BMP-2 is not attached to its carrier and is thus free to migrate away. Application of high concentrations of BMP-2 (INFUSE) can cause a dramatic increase in the rate of bone healing (up to a five-fold factor). But since it is not bound to the scaffold, unwanted side effects can occur such as bone growing in surrounding tissues which, in turn, has caused injury or even death to some patients. Other side effects can include inflammation, seroma, swelling and radiculopathy. These effects are especially serous in sensitive areas like the neck, where INFUSE is banned from such uses by the FDA.

The present disclosure relates to an enhanced collagen-based graft, which could be a collagen sponge but preferably is DBM, wherein a peptide that contains an active amino acid sequence of BMP-2 is bound to the surface of the DBM. Unlike a recombinant protein, a peptide can be produced synthetically which not only lowers the cost dramatically, but allows it to be engineered to attach directly to the carrier. Since the peptide attaches to the carrier, the problems caused by migration of the growth factor from the carrier are eliminated. Attachment to the carrier also increases the period of time that the growth factor is active in the site since its activity does not decrease as rapidly as that of a growth factor that can migrate away. Although the technology can be applied to a collagen carrier, DBM is preferred over collagen because DBM also contains other natural growth factors that work with BMP-2. Most of these additional growth factors are not present in collagen.

Described herein is a demineralized bone matrix (DBM) surface coated with a macromolecular peptide structure that has features mimicking the naturally occurring BMP-2 in bone matrix, wherein the macromolecular-peptide complex is the active ingredient. In some embodiments, the macromolecular structure having osteogenic activity is comprised of a peptide-Albumin complex (>10 peptides per Albumin molecule), wherein the peptide has Cysteine at the N-terminal to facilitate the covalent conjugation process. The Cysteine residue is followed by a flexible spacer that is followed by a functional sequence (for example an active sequence of a growth factor, any of SEQ ID NOs:1-14, or one or more fragments thereof) that has an affinity to bind BMP receptors type I and type II. The peptide is amidated on the C-terminal for protection. Some embodiments are comprised of demineralized bone matrix (DBM, which may be fully or partially demineralized) with a surface coated by effective doses of the active ingredient wherein doses range from 10 micrograms to 100 milligrams per cubic centimeter. In some embodiments, the demineralized (partially and/or fully demineralized) bone graft can be in the form of particles ranging in size from 10 microns to 10 mm. In some embodiments, the demineralized bone graft can be in the form of fibers ranging from 10 microns in diameter to 4 mm in diameter and lengths from 20 microns to 200 mm. In still other embodiments, the demineralized bone graft can be a mixture of fibers and particles. In some embodiments, the claimed DBM graft material is suitable to use by itself or mixed with one or more of another bone graft/scaffold material selected from allograft (mineralized or demineralized) or autograft bone; untreated DBM, bone marrow aspirate; a synthetic calcium phosphate, blood, gelatin; a carrier suitable to make the graft into a putty, for example PEG (polyethylene glycol), pluronic; a carrier suitable to make the graft into an injectable form, for example, glycerol, CMC (carboxymethyl cellulose). The claimed DBM graft material can constitute a minimum of 5% of the graft mixture up to 100% of the graft. In some embodiments, the claimed DBM can be incorporated into a biodegradable polymer which is then used as a graft. In some embodiments, the claimed DBM, or a graft containing the claimed DBM, can be used with other growth factors such as recombinant BMP-2, or fragments of growth factors, which can be added to the claimed DBM during manufacture or at the time of surgery. In some embodiments, the claimed DBM, or a graft containing the claimed DBM, can be used with stem cells, blood-derived concentrates or factors such as platelet rich plasma (PRP), albumin, fibrin, or any other biologic material. In some embodiments, the claimed DBM graft described above or a graft containing the claimed DBM is capable of promoting bone regeneration and repair of critical size bone defects in an animal or a human. In some embodiments, the disclosed compositions and materials may be used in procedures for use with various bone and/or soft tissue graft, for example wherein an exposed collagen surface may be intended to be in contact with and/or bound to bone. In some embodiments, the claimed DBM graft described above or a graft containing the claimed DBM is capable of promoting bone regeneration and repair of non-critical size bone defects in an animal or a human. In some embodiments, the composition may comprise a graft material comprising collagen sponge and a peptide.

BRIEF DESCRIPTION OF THE DRAWINGS

The present application file contains at least one drawing executed in color. Copies of this patent or patent application publication with color drawing(s) will be provided by the Office upon request and payment of the necessary fee

FIG. 4 depicts human BMP-2 chain sequence, with contiguous region highlighted.

FIG. 5 depicts the albumin-collagen complex (Albumin: globular shape dimer molecules colored in blue and green).

FIG. 6 is a graph of in-vitro Osteoinductivity (OI) scores based on ALP measurements.

DETAILED DESCRIPTION

Figure 1:
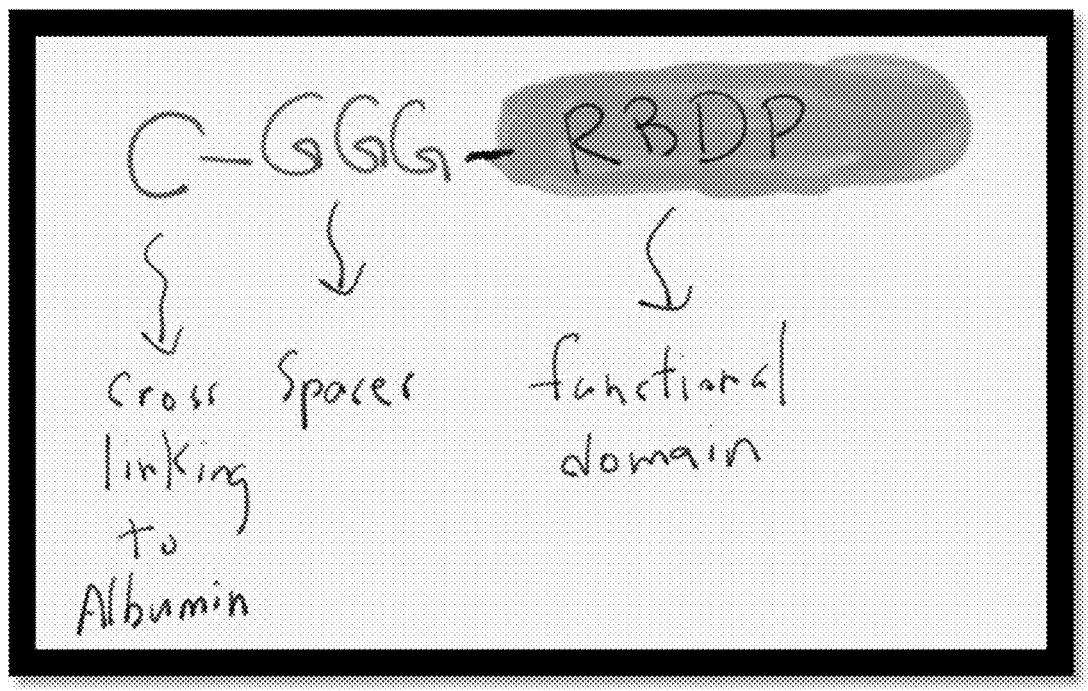
FIG. 1 depicts the basic peptide design

The peptide sequence is derived from Bone Morphogenetic Protein-2. The sequence is modified on the N terminal to allow for conjugation to Albumin (recombinant form). Cysteine residue (C) is added on the peptide's N-terminal to allow for covalent conjugation on the Albumin's Lysine residues (FIG. 1). The activated Albumin has reactive maleimide groups on its surface available for conjugation with a sulfhydryl containing peptide to form stable thioether bonds. Briefly, Albumin is reacted in isolation with a crosslinker to allow the NHS-ester end of Sulfo-SMCC (succinimidyl 4-(N-maleimidomethyl)cyclohexane-1-carboxylate) to attach at several available primary amines (side chain of lysine) on the protein surface. This reaction creates maleimide-activated Albumin, namely Albumin molecules that are labeled with several sulfhydryl-reactive maleimide groups.

Figure 2:
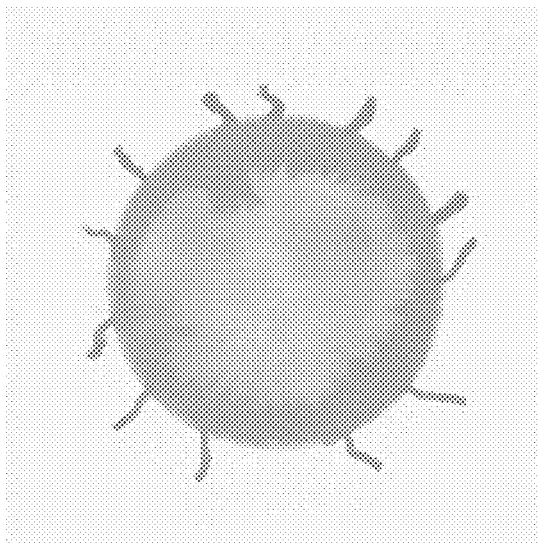
FIG. 2 depicts the albumin-peptide complex. Schematic diagram of the Albumin-peptide complex based on the globular nature of the Albumin molecule.

The Cysteine residue is followed by three Glycine (G) residues that work as a flexible spacer. The spacer is followed by the BMP-2-derived sequence (FIG. 1). This spacer is critical to allow for free movement of the peptide so that it can bind the receptor with a high affinity. Each Albumin molecule was engineered to carry at least 10 peptides (FIG. 2).

The surface of the bone allograft material (DBM and allograft bone chips) was coated with the Albumin-peptide complex. Effective doses can range from 100 microgram per CC to 100 milligram per CC, or about $0.1\text{-}100 \times 10^5$ molecules per $mm^2$.

Design Logic

The ideal design should have a peptide that can induce BMP receptor signaling, and can naturally immobilize/localize on the graft surface. BMP-2 signals via two types of receptors (BRI and BRII) that are expressed at the cell surface as homomeric as well as heteromeric complexes. The major fraction of the receptors is recruited into heterooligomeric complexes only after ligand addition. The dimer nature (i.e. multivalence) of naturally occurring BMPs is capable of receptor oligomerization.

Physiologically, BMP interactions with extracellular matrix (ECM) components facilitate localized and spatially regulated signaling; therefore, we reasoned that the lack of ECM binding in the current, clinically used forms of BMP-2 (such as INFUSE) could underlie the limited translation.

Affinity for Receptor Binding:

We analyzed the three dimensional structure of human BMP-2 and its receptor complex (2GOO) (BMP-2 dimer in complex with Type I and Type II dimers; at rcsb.org/pdb/explore/explore.do?structureId=2goo). The protein-protein interface was analyzed using a PDBePISA server (ebi.ac.uk/pdbe/pisa/). The objective was to find a contiguous region that has bonds (hydrogen bonds or salt bridges) with both types of the receptors. There was only one contiguous region (70-109) that has this unique advantage (Table 1, Table 2, and FIG. 4). We therefore designed sequences derived from this region that can bind Type I and Type II receptors and induce the needed oligomerization when presented correctly

TABLE 1

Hydrogen bonds between Type I receptor and BMP-2. Chains E and B are Type I receptors. Chains A and D are the ligands (BMP-2). Distance (Dist) is reported in Angstrom (A). Yellow highlights demonstrate the residues of interest within BMP-2 chains

| Receptor I | Dist. [Å] | Ligand |
|---|---|---|
| E:GLN 86[NE2] | 2.98 | D:LEU 51[O] |
| E:THR 55[OG1] | 2.56 | D:ASP 53[OD2] |
| E:GLN 94[N] | 2.81 | D:SER 69[O] |
| E:ARG 97[NH2] | 2.99 | D:SER 69[OG] |
| E:GLN 86[OE1] | 2.63 | D:LEU 51[N] |
| E:CYS 77[O] | 2.93 | D:ASP 53[N] |
| E:HIS 43[O] | 3.14 | D:HIS 54[NE2] |
| E:GLU 81[OE1] | 3.43 | D:ASN 59[ND2] |
| E:GLN 94[OE1] | 3.73 | D:SER 72[N] |
| E:GLN 94[OE1] | 3.39 | D:SER 72[OG] |
| B:SER 90[OG] | 2.48 | A:VAL 26[O] |
| B:LYS 92[NZ] | 3.08 | A:SER 24[O] |
| B:ASP 84[OD1] | 2.68 | A:TYR 103[OH] |
| B:ASP 84[OD1] | 3.33 | A:TYR 91[OH] |
| B:ASP 89[O] | 2.81 | A:TRP 28[NE1] |
| E:SER 90[OG] | 2.60 | D:VAL 26[O] |
| E:LYS 92[NZ] | 3.07 | D:SER 24[O] |
| E:TYR 80[OH] | 3.43 | D:LYS 101[NZ] |
| E:ASP 84[OD2] | 2.83 | D:LYS 101[NZ] |
| E:ASP 84[OD2] | 2.67 | D:TYR 103[OH] |
| E:ASP 84[OD2] | 3.19 | D:TYR 91[OH] |
| E:ASP 89[O] | 2.87 | D:TRP 28[NE1] |

TABLE 2

Hydrogen bonds between Type II receptor and the ligand (BMP-2). C and F are the Type II receptor chains. A and D are the ligand (BMP-2) chains. Distance (Dist) is reported in Angstrom (A).

| Receptor II | Dist. [Å] | Ligand |
|---|---|---|
| C:LYS 37[NZ] | 3.13 | A:GLU 109[OE2] |
| C:LEU 61[N] | 2.79 | A:SER 88[OG] |
| F:LYS 37[NZ] | 3.32 | D:SER 85[OG] |
| F:LYS 37[NZ] | 2.92 | D:GLU 109[OE1] |
| F:LYS 56[NZ] | 2.59 | D:VAL 98[O] |
| F:LEU 61[N] | 2.88 | D:SER 88[OG] |

We further modeled one of the selected peptides and generated three dimensional complexes of the peptide and the receptors (Type I and Type II). The data demonstrated that the selected sequence has high and specific affinity to bind both receptors (Table 3).

TABLE 3

Protein-protein interface data of the peptide-receptor complexes. P-value less than 0.5 indicates specific binding between the two structures.

|  | Receptor II | Receptor 1 |
|---|---|---|
| Surface A | 640 | 669.8 |
| Energy | −9.8 | −5.6 |
| P-value | 0.313 | 0.310 |
| HB | 4 | 8 |
| SB | 0 | 4 |

Figure 3:
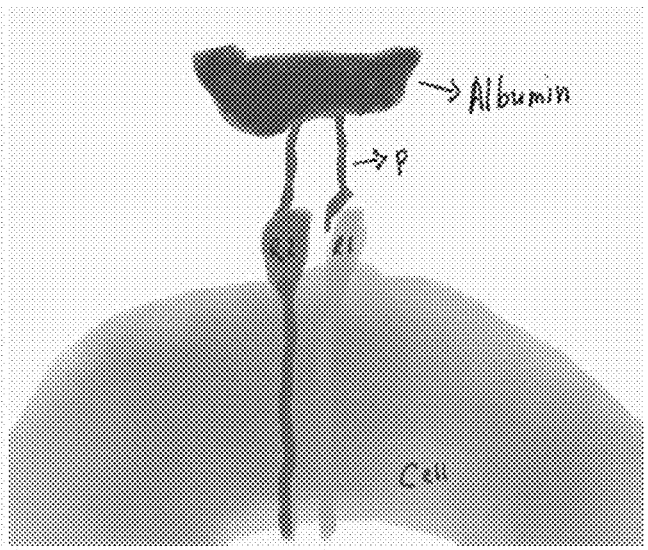
FIG. 3 depicts the albumin-peptide-cell complex. Schematic diagram of Albumin-peptide complex interacting with BMP Receptors on a single cell. P: peptide, R1: Type I receptor, R2: Type II receptor.

Receptors Oligomerization and Signaling:

Multivalent binding allows for receptors' oligomerization which is needed to initiate receptor signaling (FIG. 3). We therefore conjugated multiple peptides per Albumin molecule (for example about 10 peptides per single Albumin molecule). Successful conjugation at this ratio was confirmed through the appropriate laboratory methods, using for example without limitation, high performance liquid chromatography (HPLC). Albumin was selected for various reasons including, but not limited to, the following:

Large number of Lysine residues (about 62 per molecule; see jbc.org/content/239/3/850.full.pdf): This advantage increases the probability for successful conjugation at the desired ratio (e.g., 10 peptides per single Albumin molecule) and allows for multivalent binding between the ligand and the receptor.

Globular shape: The globular nature of Albumin is a great advantage in this design because it allows for close proximity between the peptide ligands. Close proximity aids successful receptor oligomerization and signaling (Sugio, S.; Kashima, A.; Mochizuki, S.; Noda, M.; Kobayashi, K. (1 Jun. 1999). "Crystal structure of human serum albumin at 2.5 A resolution". Protein Engineering Design and Selection. 12 (6): 439-446).

The combination of close proximity between the peptide ligands as well as multi-valent design make this macromolecule comparable to the naturally occurring growth factor ligand.

Albumin's high molecular weight (about 65 Kilo Dalton before conjugation): High molecular weight may increase the effectiveness of ligand receptor interaction and/or prolong the interaction duration. Additionally adding a large molecule like Albumin on the N-terminal may help the stabilization of the three dimensional structure of the peptide so that it can mimic the parent molecule.

Hydrophobic domains: Albumin has many hydrophobic domains which may facilitate the interaction/adhesion with cell surface Albumin is a clinically safe carrier In conclusion, the conjugation to Albumin was specifically engineered to mimic the natural ligand receptor interaction mode.

Extracellular Matrix Immobilization/Localization:

Albumin has another great advantage because it has a high binding affinity to collagen which is a major component of demineralized bone matrix (DBM).

We developed a three dimensional model for the Albumin-collagen complex (FIG. 5). We then analyzed the protein-protein interface. Data demonstrated that Albumin has a high affinity to collagen that includes a large interface area and high energy: surface area of about 2213 Å²; energy of −22.5 ΔiG kcal/mol; with 4 hydrogen bonds; and 1 salt bridge.

This natural immobilization amplifies the effectiveness of ligand-receptor binding which translates into higher levels of osteoinductivity. Amplified effectiveness could be attributed to prolonged ligand-receptor binding and the lack of or reduced receptor internalization. Prolonged signaling is an advantage when compared to soluble recombinant growth factors such as INFUSE (soluble rhBMP) which has a short half-life.

Natural immobilization confers on this design several safety advantages over soluble forms of growth factors. Soluble factors can easily escape the graft site and cause unwanted outcomes such as hetero-topic ossification, radiculopathy, or seroma and swelling.

Preparation of a Bone Graft Containing the DBM/Peptide Complex:

The albumin/peptide complex (APC) can be applied to a collagen graft (such as a collagen sponge made from bovine tendon) or preferably to DBM of animal or human origin. The APC-modified DBM or collagen can be used "as is" as a bone graft. It can be mixed with any other bone graft material either in the manufacturing plant or at the time of surgery. Such materials can include, for example, unmodified DBM, unmodified collagen, allograft or autograft bone; blood, PRP, stem cells, calcium phosphates, calcium sulfates, calcium carbonate, and natural or synthetic growth factors. The physical properties can be changed to a putty or an injectable by the addition of suitable viscosity modifiers, for example polymers such as Pluronic, CMC (carboxymethyl cellulose), PVA (poly vinyl alcohol); glycerol, gelatin, collagen. These materials can be added individually or in combination.

The modified DBM/collagen may also be incorporated into a complex with one or more biodegradable polymers, for example Poly(lactic acid)/Poly(glycolic acid) (PLA/PGA), in order to make a potentially load bearing graft.

The modified DBM/collagen is preferably aseptically processed to preserve the maximum amount of activity. It is possible, however, to terminally sterilize the modified graft product with the understanding that this process may reduce the biological activity, for example without limitation by exposure to e-beam or gamma-radiation in the presence of dry ice.

List of Peptide Sequences
 A-BMP-Derived Peptide/Linear/Synthetic

```
                                            Seq ID No. 1:
CGGGVNSKIPKACCVPTELSAISMLYLDENEKVVLKNYQDMVVE

Seq ID No. 2:
CGGGKIPKASSVPTELSAISTLYL

Seq ID No. 3:
CGGGSAISMLYLDENEKVVLKNYQDMVVE

Seq ID No. 4:
CGGGKIPKAAAVPTELSAISMLYLDENEKVVLKNYQDMVVE

Seq ID No. 5:
CGGGKIPKAAAVPTELSAISTLYL

Seq ID No. 6:
CGGGKIPKAGSVPTELSAISTLYL

Seq ID No. 7:
CGGGKIPKASGVPTELSAISTLYL

Seq ID No. 8:
CGGGKIPKAGGVPTELSAISMLYLDENEKVVLKNYQDMVVE

Seq ID No. 9:
CGGGKIPKAGSVPTELSAISMLYLDENEKVVLKNYQDMVVE

Seq ID No. 10:
CGGGKIPKASGVPTELSAISMLYLDENEKVVLKNYQDMVVE

Seq ID No. 11:
CGGGVNSKIPKACCVPTELSAISMLYLDENEKVVLKNYQDMVVE

Seq ID No. 12:
CGGGKIPKACCVPTELSAISMLYLDENEKVVLKNYQDMVVE
```

Sequence of B-Human Serum Albumin/Recombinant

```
                                            Seq ID No. 13:
MKWVTFISLLFLFSSAYSRGVFRRDAHKSEVAHRFKDLGEENFKAL

VLIAFAQYLQQCPFEDHVKLVNEVTEFAKTCVADESAENCDKSLHT

LFGDKLCTVATLRETYGEMADCCAKQEPERNECFLQHKDDNPNLPR

LVRPEVDVMCTAFHDNEETFLKKYLYEIARRHPYFYAPELLFFAKR

YKAAFTECCQAADKAACLLPKLDELRDEGKASSAKQRLKCASLQKF

GERAFKAWAVARLSQRFPKAEFAEVSKLVTDLTKVHTECCHGDLLE

CADDRADLAKYICENQDSISSKLKECCEKPLLEKSHCIAEVENDEM

PADLPSLAADFVESKDVCKNYAEAKDVFLGMFLYEYARRHPDYSVV

LLLRLAKTYETTLEKCCAAADPHECYAKVFDEFKPLVEEPQNLIKQ

NCELFEQLGEYKFQNALLVRYTKKVPQVSTPTLVEVSRNLGKVGSK

CCKHPEAKRMPCAEDYLSVVLNQLCVLHEKTPVSDRVTKCCTESLV

NRRPCFSALEVDETYVPKEFNAETFTFHADICTLSEKERQIKKQTA

LVELVKHKPKATKEQLKAVMDDFAAFVEKCCKADDKETCFAEEGKK

LVAASQAALGL
```

It is well known in the art that some modifications and changes can be made in the structure of a peptide, such as those described herein, without substantially altering the structure or sequence of that peptide, and still obtain a biologically active equivalent. In one aspect, disclosed compositions, peptides, and proteins may possess amino acid sequences that differ from the sequences disclosed herein (especially SEQ ID NOs: 1-14). In some embodiments, the amino acids may be naturally occurring or synthetic amino acids well known to those of skill in the art. In some embodiments, these differences may be accomplished by conservative amino acid substitutions of the disclosed sequences. As used herein, the term "conservative amino acid substitutions" refers to the substitution of one amino acid for another at a given location in the protein, where the substitution can be made without substantial loss of the relevant function (e.g. growth factor activity, receptor binding, etc.). In making such changes, substitutions of like amino acid residues can be made by one of skill in the art on the basis of relative similarity of side-chain substituents, for example, size, charge, hydrophobicity, hydrophilicity, and the like, and such substitutions may be assayed for their effect on the function of the protein by routine testing.

In some embodiments, the disclosed peptides and proteins may have sequence identity greater than about 60%, 65%, 70%, 75%, 80%, 85%, 90%, 91%, 92%, 93%, 94%, 95%, 96%, 97%, 98%, or 99% and less than about 100%, 99%, 98%, 97%, 96%, 95%, 94%, 93%, 92%, 91%, 90%, 85%, 80%, 75%, 70%, and 65%.

Previous attempts to use BMP derived peptides suffered from several shortcomings (mentioned above) that made it difficult for them to mimic the natural growth factor behavior. These shortcomings made it difficult to obtain reliable and reproducible effects.

In many embodiments, the disclosed compositions may be useful in procedures involving various bone and/or soft tissue grafting, for example wherein there may be an exposed collagen surface that may be intended to contact and/or bind bone. For example, bone, ligament, and tendon grafts may be performed with the disclosed composition. In many embodiments, failure of a procedure may be caused by the ends of the tendon not attaching properly to bone, and the disclosed compositions are useful in allowing such tissues to attach to bone.

EXAMPLES

Example 1; Preparation of the Graft Material

Materials and Methods:

All production operations are carried out aseptically in an ISO 6 (class 1000) clean room. DBM is made from canine cortical bone sourced from cadavers. For the study examples detailed below in this document, the source bone was canine bone. The bone is cleaned of all soft tissue, the cancellous ends are removed, and the bone is broken down into shards from which the marrow and other cellular elements are removed by purging with multiple water washes and exposure to other reagents such as antibiotics, alcohol and/or hydrogen peroxide. The bone is ground and sieved to the desired particle size (for example: 125-710 microns), then demineralized with a 0.6N HCl solution resulting in a residual calcium of <8%. After demineralization, the DBM is buffered with phosphate buffered saline, rinsed with water and either packaged directly for lyophilization or stored frozen until it can be packaged for lyophilization. Cancellous bone chips (which may be later mixed with DBM) are made from available cancellous bone (e.g., metaphyseal bone from the ends of the shafts used to make DBM). The marrow elements are removed from coarsely ground cancellous bone with multiple water washes and reagents as described above. The cleaned cancellous chips are then ground and sieved to the desired size range which may be the same or different than the corresponding DBM particles. The chips are either packaged directly for lyophilization or stored frozen until they can be packaged for lyophilization. If the allograft carrier is to be a mixture of DBM and cancellous bone chips they may be mixed prior to or after lyophilization. Typically, though non-exclusively, DBM and cancellous chips are mixed in an approximate 50/50 ratio by volume. All bone is stored lyophilized until treated with the peptide.

Recombinant human serum Albumin was obtained from Albumin Biosciences (see albuminbio.com/products.php?id=4). Peptide manufacturing and conjugation were custom manufactured at the laboratories of Bio-Synthesis (at biosyn.com). Briefly, Albumin is reacted in isolation with a crosslinker to allow the NHS-ester end of Sulfo-SMCC to attach at several available primary amines (e.g., the side chain of lysine) on the protein's surface. This created maleimide-activated Albumin. Specific peptide was combined with activated Albumin and mixed, allowing specific, linking between the maleimide group (on Albumin) and the Cysteine residue at the peptide. Albumin-peptide complex solutions were prepared at different doses sterilized by filtration and then mixed with the bone graft (about 1 ml per 1 CC graft material) for two hours at room temperature. The mixture was then incubated at 0-10 degree Celsius overnight to allow for maximum binding. On day 2, the mixture was removed from refrigerated storage and packaged for aseptic freeze-drying. At the end of freeze drying cycles, the aseptically lyophilized bone graft was vacuum sealed in impervious packaging until ready for final packaging into individual doses. At aseptic final packaging, the vacuum-sealed packets were opened and the required doses were quickly dispensed into the appropriate packaging, vacuum sealed and suitable for presentation to a sterile field for single patient use. Microbial cultures, samples for osteoinductivity and other test samples were also obtained at various stages of processing to document progress and for quality assurance purposes. These final-packaged peptide-augmented grafts and representative samples were then stored at room temperature until needed for in vivo and in vitro studies.

Example 2; Testing the Graft Osteoinductivity In Vitro

Materials and Methods:

The graft material described in Example 1 was examined for effectiveness in vitro. Control (non-coated allograft) and investigational particles (Allograft coated with Albumin-peptide complex; AAPC) were tested for inductivity using a modified Alkaline Phosphatase Assay (ALP; see Han, B., Tang, B., & Nimni, M. E. (2003). Quantitative and sensitive in vitro assay for osteoinductive activity of demineralized bone matrix. Journal of orthopaedic research, 21(4), 648-654). Briefly, C2C12 cells were cultured on the particles for 72 hours in serum-free medium and then submitted to ALP assay. The ALP assay includes the steps of: washing particles with 1×PBS twice; lysis of cells with 200 µl homogenized buffer; freeze-thaw cycle three times; transfer 30 µL of sample lysate into 96-well plate; addition of 100 µL PnPP substrate solution; incubation at 37° C. for 30 min; and then reading the plate at 405 nm and recording data. The OI Score Calculation Formula is $OI=(ALP\ test-ALP\ neg)/ALP\ neg$. This in-vitro ALP method is based on a validated mode I for assessment of OI. It is based on the ability of inductive agents to transform mesenchymal stem cells into osteoblasts in serum-free medium. To establish an expected range for an OI score in this assay for a positive control, rhBMP-2 was added to the cells, and this was comparable to the expected range for BMP-2 in the published literature.

Results:

AAPC had significantly higher OI when compared to the allograft controls (p-values=0.000). The OI of AAPC was similar to the OI of positive control cultures (i.e., BMP-2 treated cells). See FIG. 6. The data show that these surface modifications can result in substantial increases in standard markers of OI in vitro. When cells were cultured in the dish but not on the particles, the OI signal was strongly attenuated (data not shown), indicating that the majority of the induced activity occurred when the cells were in close proximity to the signal on the surface of the particles. This indicates that the presently claimed design accelerates bone healing locally without the risk of signaling molecules leaving the site. See FIG. 6.

Figure 7:
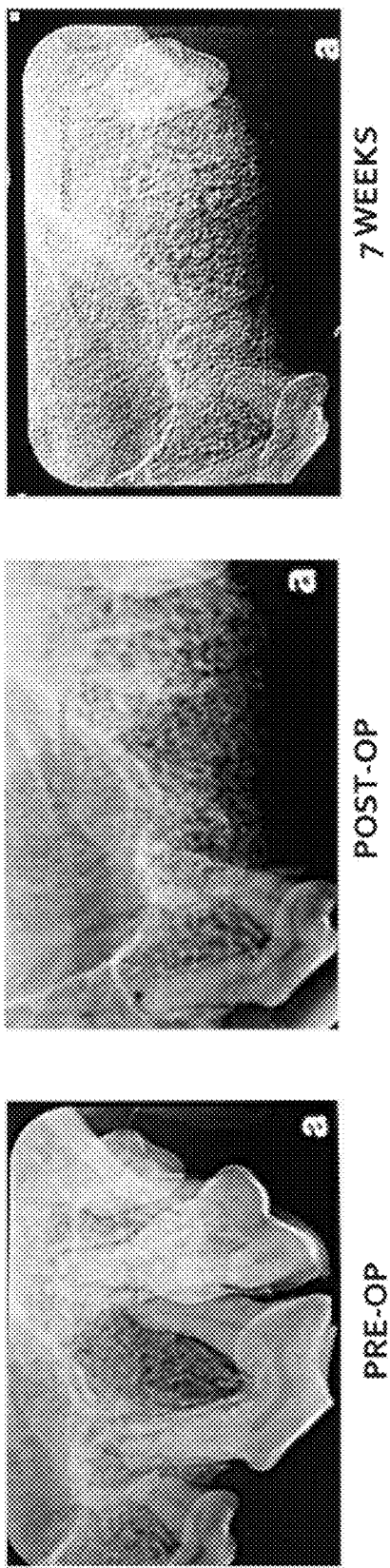
FIG. 7 depicts radiographs from a canine maxillary plate cyst case, specifically a case of radicular/periapical cyst with maxillary plate resorption XSS 208; filled with AAPC graft and covered with membrane.

Example 3; Testing the Effectiveness and Safety In Vivo: Sinus Augmentation Cases Materials and Methods:

The graft material described in Example 1 was further tested for effectiveness and safety in compassionate-use canine cases (with expected difficulties) in need of sinus or ridge augmentations. (These and in the in vivo examples described below were considered compassionate-use because in the user surgeon's estimation these were severe cases of bone loss, trauma, mal- or non-unions and other cases that came with significant expected difficulties for which other available options to preserve or restore function were not certain to produce successful results.) Standard surgical procedures were used at the discretion of the treating surgeons. The animals received one or more (0.5 CC) units of AAPC graft and were followed up until treatment outcomes had been determined. Follow up techniques included radiography and medical assessment by the treating physicians (see FIG. 7).

Results:

None of the cases had device-related events. All cases had accelerated and robust bone formation as early as two weeks. The quality of bone and soft tissue were judged to be excellent, and the success rate was 100%. Average clinical and radiographic healing was 12.2 weeks. A representative case is presented in FIG. 7.

Example 4; Maxillary Facial Reconstruction Cases

Materials and Methods:

The graft material described in Example 1 was further tested for effectiveness and safety in compassionate-use canine cases (with expected difficulties as described above) in animals with maxillary facial trauma. Standard surgical procedures were used at the discretion of the treating surgeons. The dogs received one or more (0.5 CC) units of AAPC graft and were followed up until treatment outcomes had been determined. Follow up techniques included radiography and medical assessment by the treating physicians.

Figure 8:
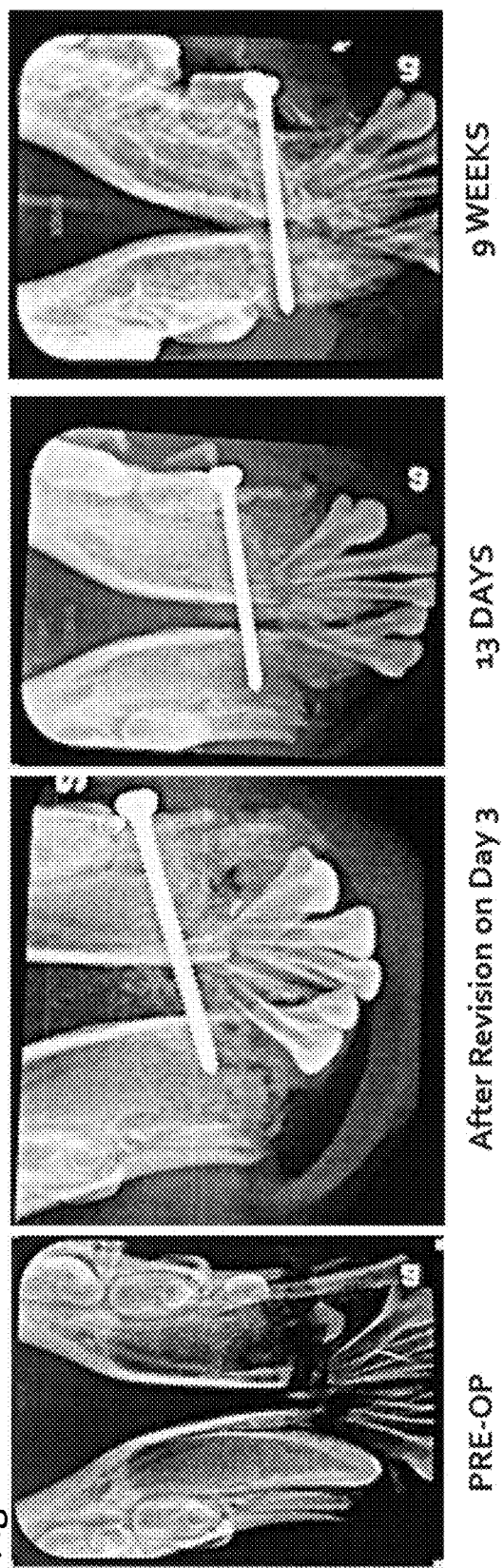
FIG. 8 depicts radiographs from a canine mandibular fracture case. Specifically, a case of bilateral mandibular fixation; separation of the rostral segment (fight trauma); Mandibular reconstruction; AAPC graft in alveoli. Additional AAPC graft was added across fracture at 3 days because patient returned with traumatic re-opening of repair.

Results:

A case of premaxilla reconstruction and two canine cases of mandibular fracture received AAPC graft due to expected clinical challenges. Despite the challenging conditions, successful healing signs were observed as early as 6 days post-op. Average time to heal (TTH) for the mandible cases was 10.5 weeks. See example in FIG. 8.

Example 5; Non-Union Cases

Materials and Methods:

The graft material described in Example 1 was further tested for effectiveness and safety in compassionate-use canine cases (with expected difficulties as described above) in animals with long bone non-unions. Standard surgical procedures were used at the discretion of the treating surgeons. The dogs received one or more (0.5 CC) units of AAPC graft and were followed up until treatment outcomes had been determined. Follow up techniques included radiography and medical assessment by the treating physicians.

Figure 9:
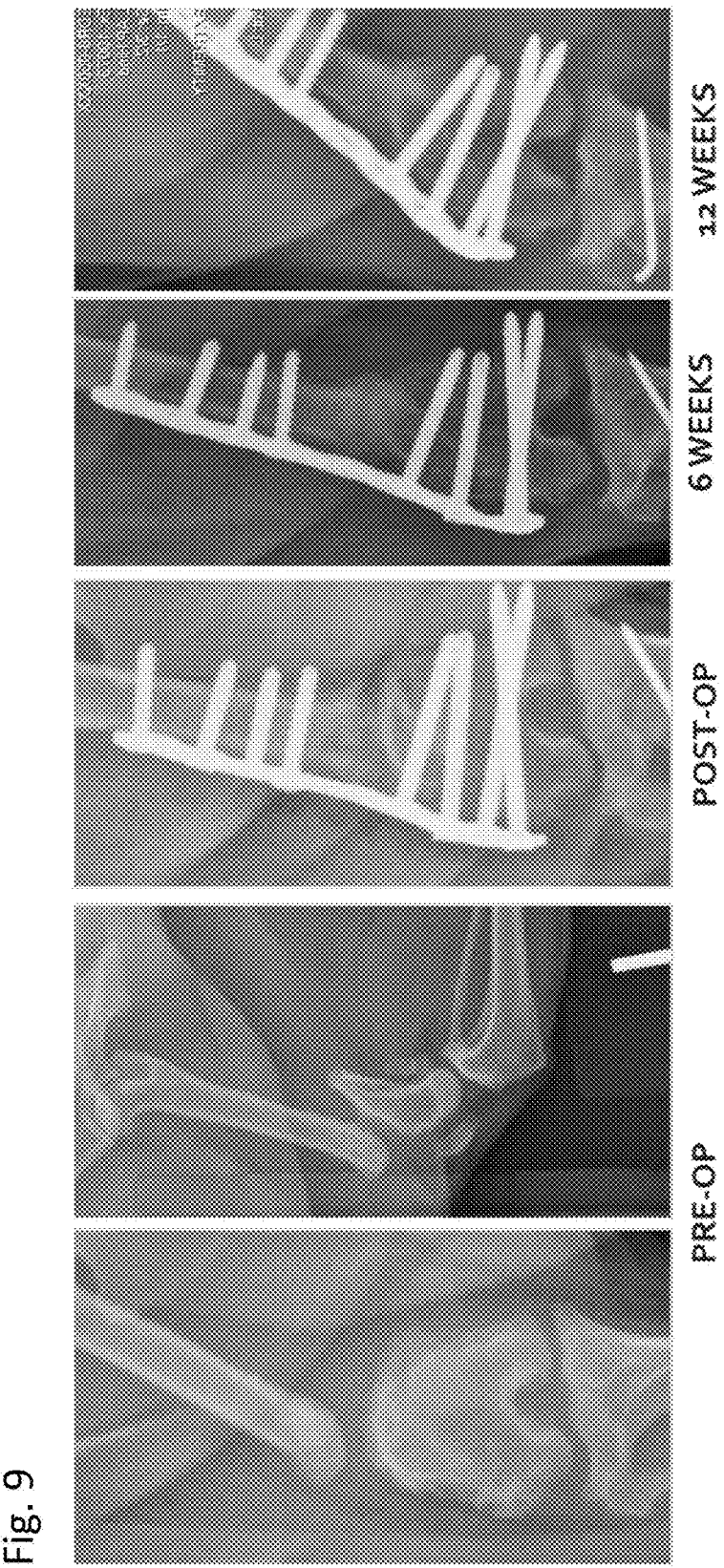
FIG. 9 depicts radiographs from a canine non-union case, specifically, a case of femoral fracture repair (neglected non-union) debrided and grafted with AACP.

Results:

Eight non-union canine cases received AAPC graft and were evaluated until completely healed. All cases had multiple risk factors that can seriously interfere with bone healing. The average TTH was 10.25 weeks. See example in FIG. 9.

Example 6: Other Compassionate Cases

The graft material described in Example 1 was further tested for effectiveness and safety in compassionate-use canine cases (with expected difficulties as described above) in animals with miscellaneous injuries including acute fracture (1 case), comminuted fractures (3 cases), joint fusion, and TPLO revision (3 cases). Standard surgical procedures were used at the discretion of the treating surgeons. The dogs received one or more (0.5 CC) units of AAPC graft and were followed up until treatment outcomes had been determined. Follow up techniques included radiography and medical assessment by the treating physicians.

Figure 10:
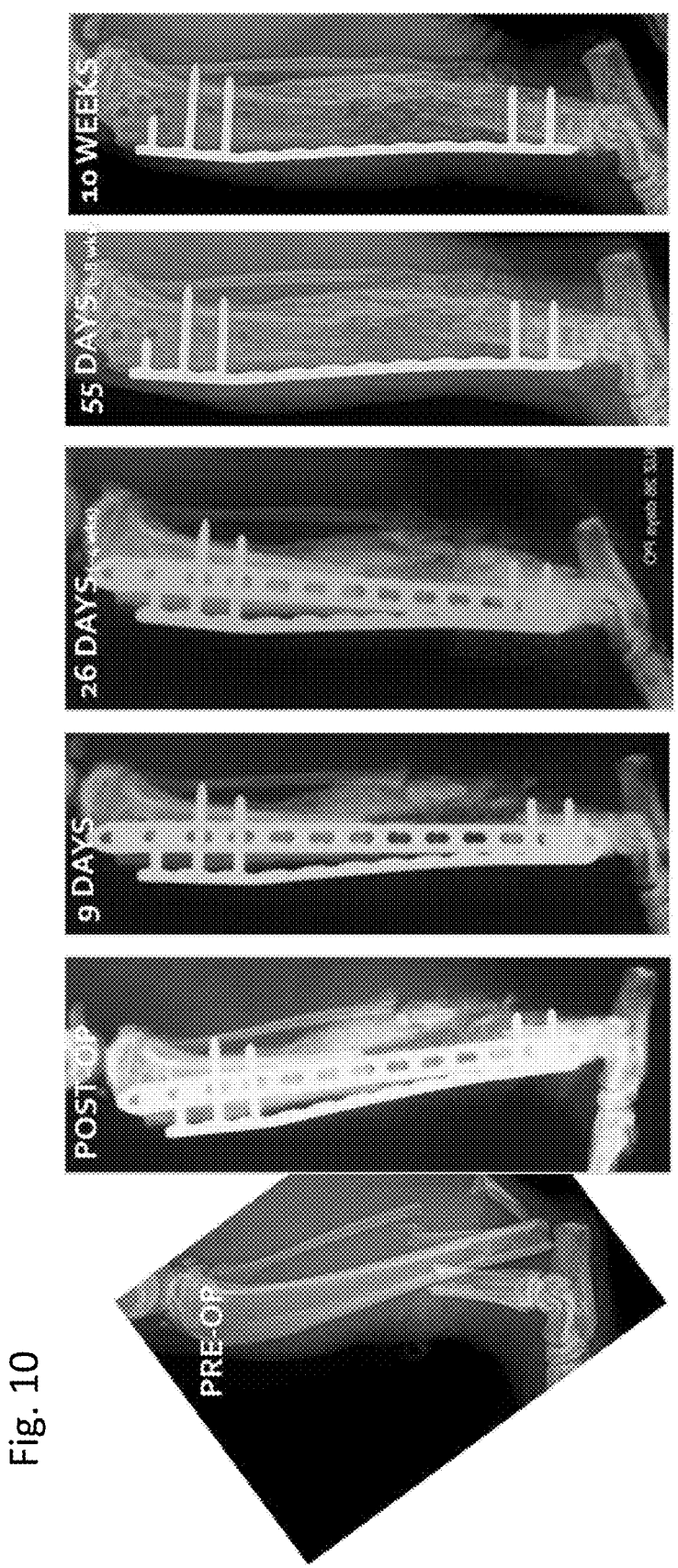
FIG. 10. depicts radiographs from a feline comminuted fracture repair, specifically, a case of comminuted fracture repair filled with the AAPC graft.

Results:

Average TTH are available in Table 5. A representative case of a comminuted fracture is seen in FIG. 10.

Example 7, Summary of Clinical Experience

TABLE 4

High-level summary of Time-to-Heal (TTH) in various indications

| Procedure | Number of | Time to Healing (TTH, Mean), |
|---|---|---|
| Acute fracture | 1 | 12 |
| Comminuted Fractures | 3 | 8.3 |
| Joint Fusion | 1 | 6 |
| Non-union | 8 | 10.25 |
| TPLO revision | 3 | 15 |
| Sinus augmentation | 10 | 12.2 |
| Maxillary reconstruction | 1 | 5 |
| Mandibular | 2 | 10.5 |

No device-related events were observed in any of the cases. The accelerated robust new bone formation was reported in all cases and the time needed for healing was not inferior to historical BMP-2 data from similar cases (Example 8). These preliminary data are very encouraging and suggest a potential alternative for autograft and BMP-2.

Example 8; Time to Heal (TTH); Comparison to rhBMP-2 (Historical Data in Animals)

Figure 11:
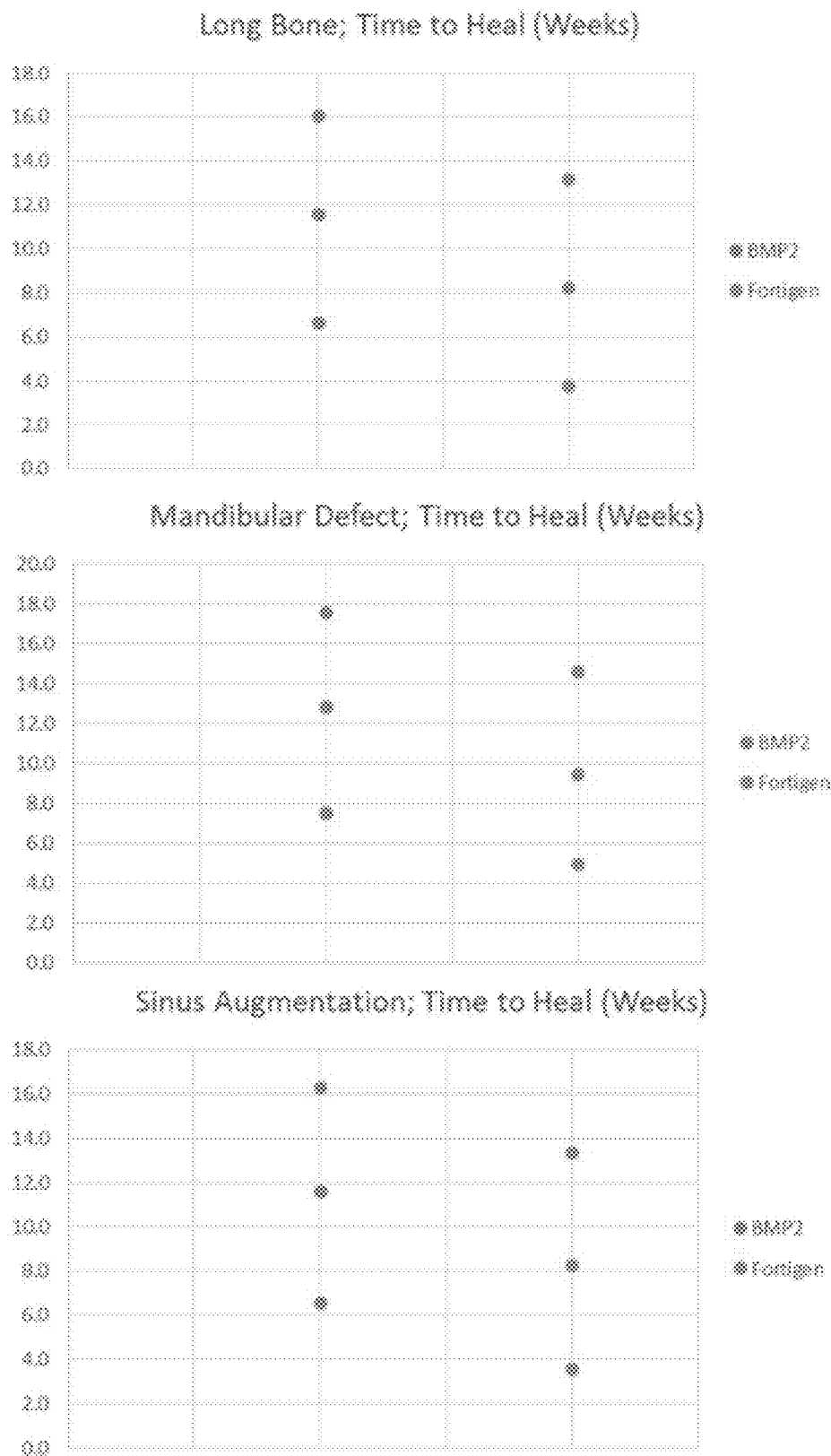
FIG. 11. depicts time to heal (TTH) comparisons to rhBMP2 for Long Bone, Mandibular Defect, and Sinus Augmentation studies.

BMP's historical data were based on Cory B. et al., CVJ/VOL 53/JULY 2012. We compared TTH data using Bayesian simulation approach. Data are expressed as credible intervals of TTH. AAPC's TTH is short and not inferior to BMP's healing time FIG. 11 (below).

While multiple embodiments are disclosed, still other embodiments of the present invention will become apparent to those skilled in the art from the following detailed description. As will be apparent, the disclosed compositions and methods are capable of modifications in various obvious aspects, all without departing from the spirit and scope of the present disclosure. Accordingly, the detailed description is to be regarded as illustrative in nature and not restrictive.

All references disclosed herein, whether patent or non-patent, are hereby incorporated by reference as if each was included at its citation, in its entirety. In case of conflict between reference and specification, the present specification, including definitions, will control.

Although the present disclosure has been described with a certain degree of particularity, it is understood the disclosure has been made by way of example, and changes in detail or structure may be made without departing from the spirit of the disclosure as defined in the appended claims.

The invention claimed is:

1. A demineralized bone matrix (DBM) composition comprising: DBM; and a surface coating on the DBM of a macromolecular-peptide structure, wherein the macromolecular-peptide comprises a peptide conjugated to a protein at a ratio of about 10 peptides to 1 protein, and results in bone growth in vivo and mimics naturally occurring bone morphogenic protein (BMP)-2, wherein the macromolecular-peptide is the active ingredient, wherein the peptide is of SEQ ID NO:6, and wherein the protein is albumin.

2. The DBM composition of claim 1, wherein the peptide has Cysteine at the N-terminus to facilitate covalent conjugation.

3. The DBM composition of claim 2, wherein Cysteine residue is followed by a flexible spacer.

4. The DBM composition of claim 3, wherein the flexible spacer comprises one or more amino acid residues.

5. The DBM composition of claim 4, wherein the flexible spacer comprises the amino acid glycine.

6. The DBM composition of claim 1, wherein the peptide is amidated at the C-terminus for protection.

7. The DBM composition of claim 1, wherein the peptide concentration is from 10 micrograms to 100 milligrams per cubic centimeter.

8. The DBM composition of claim 1, having an average particle size ranging from 10 microns to 10 mm.

9. The DBM composition of claim 1, wherein the composition comprises fibers ranging from 10 microns in diameter to 4 mm in diameter.

10. The DBM composition of claim 1, wherein the composition comprises fibers with lengths from 20 microns to 200 mm.

11. The DBM composition of claim 1, wherein the composition comprises fibers and particles.

12. The DBM composition of claim 1, further comprising one or more of bone graft/scaffold material selected from allograft or autograft bone; cancellous bone; untreated DBM; bone marrow aspirate; a synthetic calcium phosphate; blood or blood-derived concentrates; gelatin; PEG; pluronic; glycerol; and carboxymethyl cellulose (CMC).

13. The DBM composition of claim 1, wherein the percentage, by weight, of DBM in the composition is 5% to 99.5% of a total weight of the composition.

14. The DBM composition of claim 1, further comprising a biodegradable polymer.

15. The DBM composition of claim 1, further comprising one or more growth factors.

16. The DBM composition of claim 15, wherein the growth factor is recombinant BMP-2.

17. The DBM composition of claim 1, further comprising one or more of stem cells, platelet rich plasma (PRP) blood, calcium phosphates, calcium sulfates, calcium carbonate, synthetic growth factors, natural growth factors, collagen, and fibrin.

18. The DBM composition of claim 1, wherein the composition comprises a collagen sponge.

19. The DBM composition of claim 1, wherein the DBM is derived from an animal or human.

20. The DBM composition of claim 19, wherein the DBM is derived from a canine.

21. The DBM composition of claim 19, wherein the DBM is derived from a human.

22. A method of manufacturing the DBM composition of claim 1, comprising: conjugating a plurality of peptides of SEQ ID NO:6 to albumin at a ratio of about 10 peptides to 1 albumin to create macromolecular-peptides; combining the macromolecular peptides with a DBM;
  coating the surface of the DBM with the macromolecular-peptides; and thereby creating a bone repair composition for supporting bone growth in vivo that mimics naturally occurring BMP.

23. A method of repairing a damaged bone or a defect in a bone of a subject, the method comprising:
  applying the DBM of claim 1 to the bone of the subject.

24. The method of claim 23, wherein the subject is a human.

25. The method of claim 23, wherein the subject is a mammal.

26. The method of claim 23, wherein the subject is a canine.

\* \* \* \* \*

UNITED STATES PATENT AND TRADEMARK OFFICE
CERTIFICATE OF CORRECTION

| | | |
|---|---|---|
| PATENT NO. | : 11,565,025 B1 | Page 1 of 1 |
| APPLICATION NO. | : 15/687199 | |
| DATED | : January 31, 2023 | |
| INVENTOR(S) | : Abdulhafez Abdulwahed Abdulhafez, Helen Newman and Lawrence Shimp | |

It is certified that error appears in the above-identified patent and that said Letters Patent is hereby corrected as shown below:

In the Specification

At Column 4, Line 56:
"or about $0.1\text{-}100\times10^{5}$"
Should be:
--or about $0.1\text{-}100\times10^{15}$--

Signed and Sealed this
Twenty-first Day of March, 2023

*Katherine Kelly Vidal*

Katherine Kelly Vidal
*Director of the United States Patent and Trademark Office*